United States Patent
Siess

(10) Patent No.: US 7,011,620 B1
(45) Date of Patent: Mar. 14, 2006

(54) INTRAVASCULAR BLOOD PUMP

(75) Inventor: Thorsten Siess, Wuerselen (DE)

(73) Assignee: Impella CardioSystems AG, (DE)

( * ) Notice: Subject to any disclaimer, the term of this patent is extended or adjusted under 35 U.S.C. 154(b) by 413 days.

(21) Appl. No.: 10/148,792

(22) PCT Filed: Nov. 3, 2000

(86) PCT No.: PCT/EP00/10863

§ 371 (c)(1),
(2), (4) Date: Jun. 4, 2002

(87) PCT Pub. No.: WO01/39817

PCT Pub. Date: Jun. 7, 2001

(30) Foreign Application Priority Data

Dec. 4, 1999 (DE) .......................... 299 21 352 U

(51) Int. Cl.
*A61N 1/362* (2006.01)
(52) U.S. Cl. ...................................................... 600/16
(58) Field of Classification Search ............. 600/16–18
See application file for complete search history.

(56) References Cited

U.S. PATENT DOCUMENTS

| | | | |
|---|---|---|---|
| 5,290,227 A | * | 3/1994 | Pasque .......................... 600/16 |
| 5,438,997 A | | 8/1995 | Sieben et al. |
| 5,460,889 A | * | 10/1995 | Gross et al. ................. 428/416 |
| 5,851,174 A | | 12/1998 | Jarvik et al. |
| 5,911,685 A | * | 6/1999 | Siess et al. .................... 600/16 |
| 5,919,162 A | | 7/1999 | Burns |

FOREIGN PATENT DOCUMENTS

| | | |
|---|---|---|
| DE | 196 22 335 | 12/1997 |
| EP | 0 764 448 | 3/1997 |
| EP | 0764448 A2 | 3/1997 |
| WO | WO 97/37696 | 10/1997 |
| WO | WO 97/37696 A1 | 10/1997 |
| WO | WO 98 44619 | 10/1998 |
| WO | WO 98/44619 A1 | 10/1998 |

* cited by examiner

Primary Examiner—Scott M. Getzow
(74) Attorney, Agent, or Firm—Fulwider Patton LLP

(57) ABSTRACT

An intravascular blood pump designed to be advanced through the blood vessel system of the patient, comprises a housing (15) accommodating an electric motor (12), the proximal end of the housing (15) being connected to a catheter (23) and the distal end thereof carrying a pump (11). The electric motor (12) includes a stator winding (17) forming a load-bearing component of the housing (15). The stator winding (17) is embedded in a matrix made of synthetic resin. The housing (15) is of an ironless design without any magnetic reflux device. The motor is operated with a rotational speed of about 50,000 upm. The magnetic stray field generated with such high frequencies does not disturb the cardiac rhythm of the patient. The motor can be given a compact size and thus has a high mechanical output power.

10 Claims, 3 Drawing Sheets

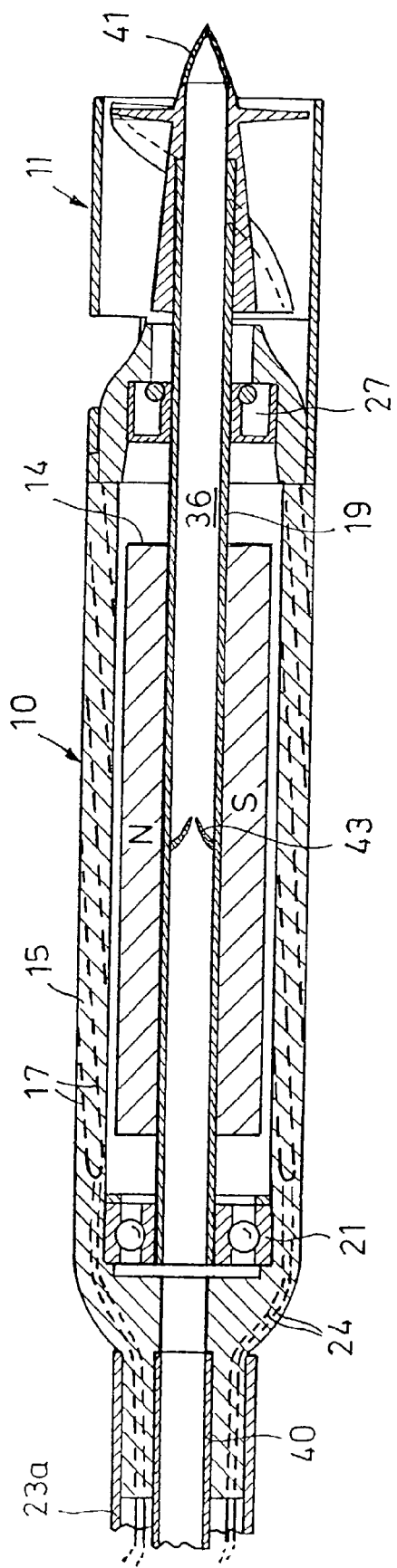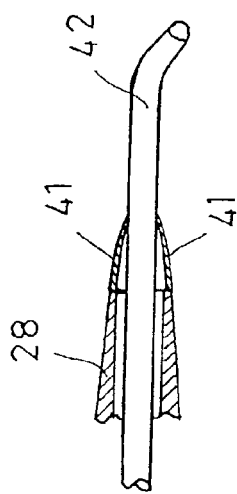

INTRAVASCULAR BLOOD PUMP

Figure 1:
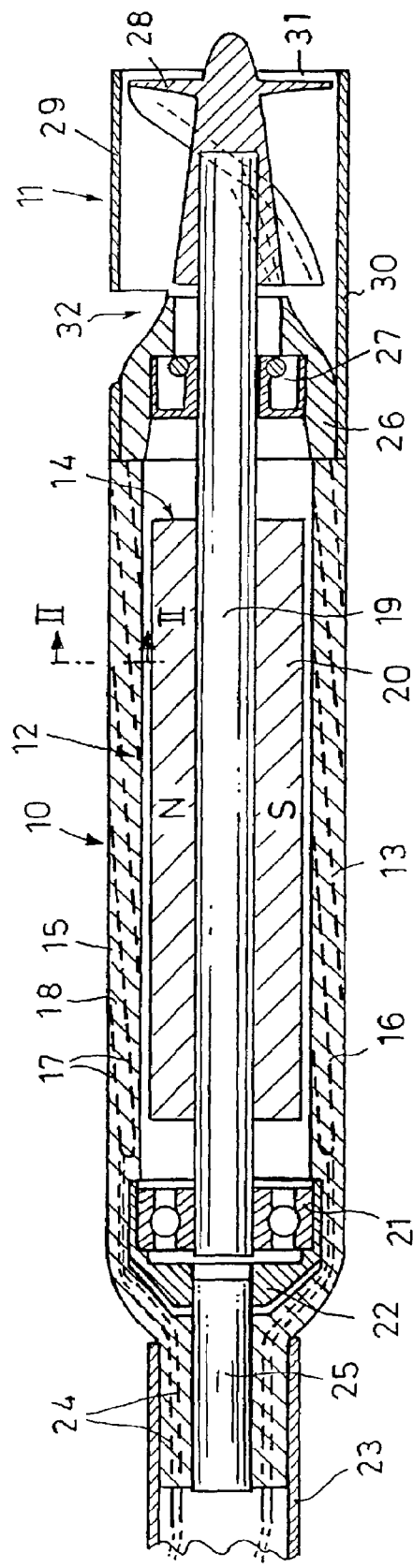

The invention relates to an intravascular blood pump comprising a housing accommodating an electric motor, with the proximal end of the housing being connected to a catheter and the distal end thereof carrying a pump. An intravascular blood pump is a blood pump which can be advanced through the vessel system of a patient so as to be operated in the heart of the patient or at another site of the body.

From WO/44619, an intravascular blood pump is known which fulfills the above conditions. This blood pump comprises a housing having a diameter of 7 mm at maximum and accommodating an electric motor arranged to drive the impeller of a pump. The electric motor comprises a stator with internal windings and external magnetic reflux metal-sheets. The reflux metal-sheets are cast together with the stator winding in a housing made from plastic. The reflux metal-sheets function to concentrate the magnetic flow of the circulating magnetic field and to increase the efficiency of the electric motor by avoiding magnetic dissipation losses.

DE 196 22 335 A1 describes a balloon catheter comprising a pump which is driven by a motor arranged along the length of the catheter tube. A guide channel for a guide wire is arranged to extend through the catheter tube and coaxially through the pump. In this manner, the balloon catheter can be shifted together with the pump onto an already set guide wire for positioning the pump at the desired site in the patient's body.

U.S. Pat. No. 5,851,174 and EP 0 764 448 A2 each describe a cardiac support device comprising an intracardiac blood pump provided to be introduced into the heart through an incision site. The blood pump has an outer diameter of 9 to 12 mm. This fails to meet the demands posed to an intravascular blood pump. The motor comprises a stator, integrated into the housing and having a stator winding, and a magnetic rotor. The rotor is provided with blades projecting into the annular space between the stator and the rotor. For this reason, the annular space must have a large width, causing the magnetic air gap between the rotor and the stator to become larger and reducing the performance of the motor and its efficiency, respectively.

An intravascular blood pump wherein the drive unit is integrated with the pump member must have the smallest possible maximum outer diameter and a small rigid length. As of yet, no successful effort has been made to design a blood pump suitable to operate with the required efficiency while having an outer diameter of less than 5 mm. An intravascular blood pump is required to be capable of a delivery rate of 1.5 liters per minute for physiological pressures (60 to 80 mm Hg).

It is an object of the invention to provide an intravascular blood pump which allows for a still further miniaturization so that the pump can be advanced through the vessel system easily and safely.

According to the instant invention, the above object is achieved by the features indicated in claim 1. A special characteristic of the blood pump of the invention resides in that the stator of the electric motor is of an ironless design without any magnetic reflux device and that the stator winding is a structural component of the motor housing. According to the invention, the structural component of the motor housing is formed by a stator winding embedded into a matrix made of synthetic resin. The current flowing in the stator winding generates a circulating magnetic field to be followed by the movement of the magnet device attached to the rotor. The omission of pole pieces and an ironclad reflux device will have the effect that the magnetic field generated in the stator winding is not bundled externally of the stator winding, thus causing dissipation losses towards the outside. Tests performed under special consideration of this effect have revealed that the magnetic field circulating at a high rotational speed does not have a detrimental influence on the cardiac rhythm of the patient. The rotational speed of the magnetic field and thus also of the electric motor is in the magnitude of 50,000 rpm and will in any case be higher than 30,000 rpm. With such a high rotational speed, the rotating magnetic field has no harmful effects in the patient's body. In the blood pump of the invention, the place for a reflux device is saved. Thus, the rotor can be given a larger diameter, consequently allowing for an increase of the moment of rotation. Further, magnetic-reversal losses which would occur in a magnetic reflux device consisting of iron, are avoided. Thus, with the above mentioned high rotational speeds, the increased dissipation losses will be more than compensated for. Further, also the weight of the motor is reduced. The ironless design of the stator makes it possible to use a larger wire thickness for the stator winding so that the current intensity can be increased while the ohmic losses in the stator winding will remain small.

In the blood pump of the invention, the housing containing the electric motor can be reduced to an outer diameter of about 4 mm, which corresponds to a catheter of 12 F (F=French). The rigid axial length of the overall pump, i.e. of the motor housing and the pump unit, can be reduced to $\leq 20$ mm. Thus, the intravascular blood pump can be advanced through the blood vessel system of the patient and be placed at the desired site. The dimensions also make it possible to maneuver the blood pump in an unobstructed and controlled manner through the arcus aortae.

The stator winding occupies at least 70%—preferably at least 80%—of the wall thickness of housing. The stator winding together with the resinous matrix forms the load-bearing structural part of the housing wall. Generally, it will be sufficient to form the housing by the stator winding in combination with the resinous matrix. It appears suitable, however, to provide the inner side of the housing wall with a protective insulation layer which would also serve to protect the winding from friction and thus prevent the rotor from damaging the winding upon mechanical contact. Further, the outer side of the housing can be provided with an additional protective foil, which foil must have good heat-conducting properties to transfer the heat generated in the stator winding to the blood flowing along on the outside.

For setting the blood pump together with the complementary catheter by use of the Seldinger technique, the blood pump must comprise a guide channel designed for passage of a guide wire therethrough. The blood pump can then be advanced along the guide wire in the vessel system of the patient. The blood pump of the invention is suitably provided with a guide channel of the above type which is arranged to pass through the shaft of the rotor and through the axis of the impeller of the pump. Corresponding sealing elements can be provided to safeguard that blood leaking into the guide channel will not enter into the catheter arranged proximally of the housing, and intrude into the mechanics of the pump.

Embodiments of the invention will be explained in greater detail hereunder with reference to the drawings.

Figure 2:
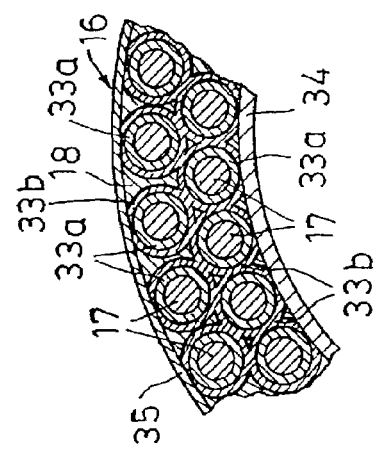
Figure 3:
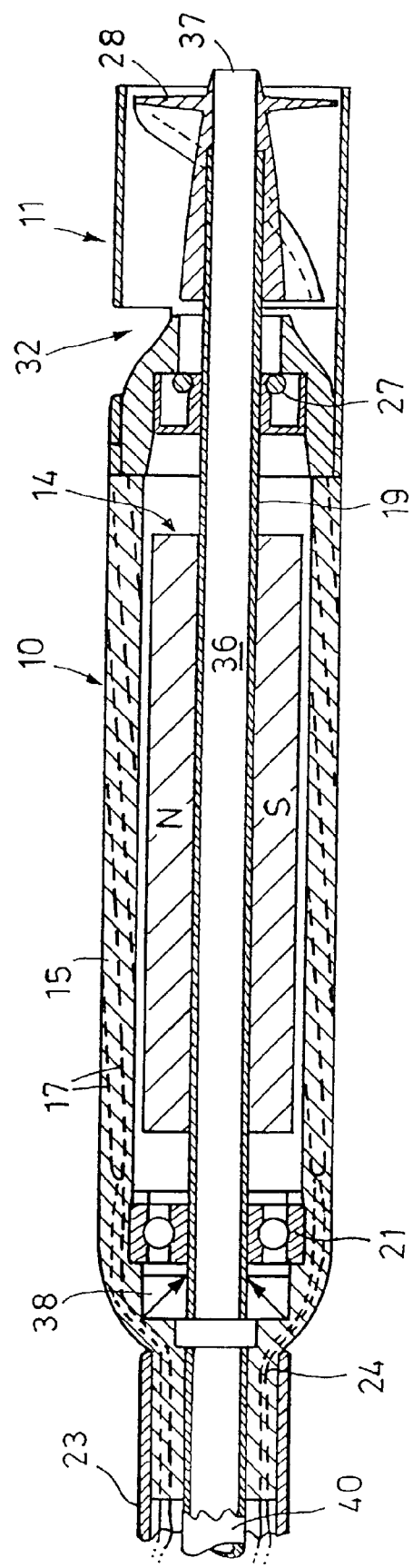

FIG. 1 is a longitudinal view of a first embodiment of the intravascular blood pump with a solid shaft, FIG. 2 is a cross-sectional view through the housing wall, taken along the line II—II in FIG. 1, FIG. 3 is a longitudinal view of a second embodiment of the blood pump, comprising a guide channel for a guide wire, FIG. 4 is a view of a modification of the pump of FIG. 3 with a modified sealing arrangement for sealing the guide channel, and FIG. 5 is a view of the sealing arrangement of FIG. 4 with a guide wire inserted therethrough.

The blood pump illustrated in FIG. 1 comprises a motor unit 10 and a pump unit 11. The motor unit 10 comprises an electric motor 12 including a stator 13 and a rotor 14. The stator 13 also forms the outer wall of the housing 15, i.e. there exists no additional housing surrounding the stator. The housing wall 16 forming the stator 13 comprises a stator winding 17 made from wires embedded into a synthetic-resin matrix 18. The winding 17 is a so-called basket winding with wires extending obliquely in the longitudinal direction of housing 15. Stator winding 17 includes a plurality of coils, distributed along its periphery and connected to each other in a star-shaped or triangular configuration, which are actuated successively to generate a circulating magnetic field. The sensor-free commutation of these coils is performed through an extracorporeal control device connected to the motor by a multi-core wire line 24. Winding 17 is activated in a manner causing the circulating magnetic field to rotate with a rotational speed of 50,000 rpm.

Rotor 14 comprises a permanent magnet 20 mounted to shaft 19, with the magnet having its north pole N arranged on one side of its periphery and its south pole S on the other side of its periphery.

On the proximal end, shaft 19 is supported in a ball bearing 21. The ball bearing is held in a cap 22 arranged to close the proximal end of housing 15. The proximal end of housing 15 is joined by the catheter 23 which comprises a flexible tube. Extending through the wall of catheter 23 are the feed lines 24 for stator winding 17. In the present embodiment, the housing cap 22 is connected to a projection member 25 projecting into catheter 23 to obtain high mechanical stability.

The distal end of housing 15 is terminated by a transition piece 26 which also includes a sealing 27 serving as a shaft bearing. Shaft 19 extends through this sealing into pump unit 11 where the impeller 28 is attached to the distal end of the shaft. Impeller 28 rotates in the cylindrical pump housing 29 which is connected to housing 15 by at least one web 30 arranged in the longitudinal direction. Pump unit 11 is designed for suctional intake of blood via the axial intake opening 31 and for conveyance in the axial direction, the blood issuing laterally from the openings 32 and flowing axially along housing 15 so that the flow heat is carried off from housing 15. Alternatively, the pump can also be operated in the opposite sense.

In the embodiment according to FIG. 1, shaft 19 is a solid shaft. The rigid length of the overall blood pump along the motor unit and the pump unit 11 is about 20 mm. The maximum outer diameter is 4 mm.

The wires of winding 17 embedded into the resinous matrix 18 of housing wall 16 without intermediate cavities are illustrated in FIG. 2. These wires are surrounded by an insulating sheath 33a. The insulating sheaths in turn are coated with stoving paint 33b. After manufacture of the stator winding 17, the wires are bonded to each other while subjected to heat; in the process, the stoving paint layers of adjacent wires will be fused to each other and thus form a fixed wire structure. This wire structure, while placed in an injection mold, will subsequently be enmolded by the synthetic resin 18 which is an epoxide resin. This compound comprising the winding and the epoxide resin is of high mechanical stability so that the stoving paint 33b serves exclusively for the preliminary fixation of the wires of the winding so as to facilitate the handling of the coil during the manufacture process. The stoving paint can be formed with correspondingly thin walls, thus allowing to obtain an optimum relation between copper, stoving paint, insulation and epoxide resin. Notably, it is only the percentage of the copper in the winding which is decisive for the efficiency of the motor.

After the housing 15 has been produced in the above manner, the catheter 23 can be attached to the housing. Bearing 21 has an outer diameter smaller than the inner diameter of housing 15 and thus can be inserted into the housing from the distal end.

The inner side of housing wall 16 is provided with a thin insulation layer 34 of a captone foil (polyimide) having a strength of 12 to 25 µm. This insulating layer serves for insulating the wires and protecting them from friction and thus preventing damage caused by the rotor, and further acts as a slide layer.

Arranged on the outer side of housing wall 16 is an cover foil 35 of a material with good heat conductivity, preferably of a metal such as titanium. By way of alternative to such a cover foil, the resinous matrix 18 can be widened towards the outside.

The matrix 18 of synthetic resin comprises a duromer with a portion of at least 50 percent by weight of $Al_2O_3$ to increase heat transfer to the outside. The thickness of housing wall 16 inclusive of the layers 34 and 35 is about 0,3 mm. The stator winding 17 occupies at least 70% and preferably at least 80% of the wall thickness of housing wall 16.

The motor is of the toothless type, i.e. it is not provided with circumferentially distributed pole pieces with windings held thereon. Instead, the stator winding is integrated into the wall of tubular housing 15 and, in this region, considerably contributes to the mechanical stability of housing wall 16.

The embodiment according to FIG. 3 is different from the first embodiment in that the shaft 19 is formed as a hollow shaft and includes a guide channel 36 extending along the complete length of the shaft. Guide channel 36 communicates with the lumen of catheter 23 via a further tube 40.

The distal end of shaft 19 is formed with an opening 37. Via this opening, blood might leak into the guide channel 36. To keep this blood from advancing into the interior of the electric motor, a sealing 38 is provided proximally of bearing 21.

The blood pump according to FIG. 3 can be shifted over a guide wire (not shown) which extends through catheter 23 and guide channel 36 and is beforehand placed in the patient's body. Except for this modification, the structural features and effects described in connection with the first embodiment apply also to the embodiment of FIG. 3.

The embodiment shown in FIGS. 4 and 5 likewise comprises a hollow shaft 19 extending through the motor unit 10 and the pump unit 11 and forming a guide channel 36 for a guide wire. The proximal end of shaft 19 is joined by a tube 40 passing through catheter 23, which tube is connected to housing 15 and does not rotate along with shaft 19.

On the distal end of guide channel 36, a sealing 41 is provided for sealing the guide channel 36. This sealing 41 is a self-closing lip sealing. An opening is formed in the sealing for the passage of guide wire 42 therethrough. FIG. 5 does not illustrate the manner in which the guide wire 42 has pushed open the opening of sealing 41. Guide wire 42 can thus be axially displaced within sealing 41. When withdrawn in the proximal direction, the guide wire will automatically close the sealing 41.

A corresponding self-closing sealing 43 is arranged internally of shaft 19. This sealing 43 is provided for additional sealing effect. The lumen of guide channel 36 has a diameter of 0.6 mm, thus allowing passage therethrough of a guide wire of a corresponding diameter.

What is claimed is:

1. An intravascular blood pump comprising an elongate housing accommodating an electric motor, the proximal end of the housing being connected to a catheter and the distal end thereof carrying a pump, the electric motor comprising a stator winding, embedded in matrix made from synthetic resin, and a bladeless magnetic rotor supported for rotation, wherein the embedded stator winding exclusively forms a load-bearing component of the housing, the housing being devoid of iron and of any magnetic flux device.

2. The blood pump of claim 1, wherein the housing has a wall thickness and the stator winding occupies at least 70% of the wall thickness of housing.

3. The blood pump of claim 2, wherein the wall thickness of the housing is smaller than 0.5 mm.

4. The blood pump of claim 1, characterized in that the electric motor comprises a hollow shaft and that the axis of the impeller of the pump is formed with a guide channel for a guide wire.

5. The blood pump of claim 1, further comprising seals arranged at the distal end and the proximal end of the housing between the housing and the shaft.

6. The blood pump of claim 4, further comprising a seal arranged at the distal end of the housing between the housing and the shaft, and at least one further seal arranged in the course of the guide channel and allowing passage of the guide wire therethrough.

7. The blood pump of claim 1, wherein the inner side of the housing has arranged thereon an insulating layer protecting the stator winding.

8. The blood pump of claim 1, wherein the outer side of the housing has arranged thereon a cover layer protecting the stator winding and providing for electric insulation and heat dissipation.

9. The blood pump of claim 1, wherein wires of the stator winding are provided with an insulating sheathing surrounded by a stoving paint layer.

10. The blood pump of claim 4, wherein the proximal end of the hollow shaft is supported in a bearing having an outer diameter smaller than the inner diameter of the stator.

* * * * *